United States Patent [19]
Aoki et al.

[11] Patent Number: 5,968,835
[45] Date of Patent: Oct. 19, 1999

[54] METHOD FOR ESTIMATING NITRIC ACID AND NITROUS ACID IONS

[75] Inventors: Toyoaki Aoki, Hirakata; Hiroshi Tsugura, Tokyo, both of Japan

[73] Assignee: Kabushiki Kaisha Meidensha, Tokyo, Japan

[21] Appl. No.: 08/807,523

[22] Filed: Feb. 27, 1997

Related U.S. Application Data

[63] Continuation of application No. 08/458,795, Jun. 2, 1995, Pat. No. 5,668,014.

[30] Foreign Application Priority Data

Jun. 6, 1994 [JP] Japan .................................. 6-122903
Apr. 28, 1995 [JP] Japan .................................. 7-105115

[51] Int. Cl.$^6$ .......................... G01N 33/00; G01N 33/18; G01N 35/08; G01N 21/70
[52] U.S. Cl. .............................. 436/110; 436/52; 436/53; 436/106; 436/108; 436/110; 436/111; 436/113; 436/114; 436/172
[58] Field of Search ..................... 436/106, 108, 436/110, 111, 113, 114, 172, 52, 53; 422/52, 81, 82

[56] References Cited

U.S. PATENT DOCUMENTS

| | | | |
|---|---|---|---|
| 3,877,875 | 4/1975 | Jones et al. .......................... | 436/114 X |
| 4,268,279 | 5/1981 | Shindo et al. ............................... | 55/16 |
| 4,412,006 | 10/1983 | Cox et al. ................................ | 436/110 |
| 5,300,441 | 4/1994 | Fujinari et al. .......................... | 436/110 |

FOREIGN PATENT DOCUMENTS 56-070804 6/1981 Japan .

OTHER PUBLICATIONS

T. Aoki et al. Anal. Chim. Act (1995), 308 (1–3), pp. 308–312.

Garside, "A Chemiluminescent Technique For The Determination Of Nanomolar Concentrations Of Nitrate And Nitrite In Seawater", *Marine Chemistry*, vol. 11:159–167, (1982).

Gerth, "Microassay For Ammonium By Determination Of Ammonia Nitrogen In A Nitrogen Analyzer", *Analytical Biochemistry*, vol. 144:432–435, (1985).

P. R. Kraus et al., *Anal. Lett.* 1987, 20, 183–200.

Halvatzis et al., "Continuous–Flow Chemiluminometric Determination Of Ammonium Ion In Fertilizers", *Talanta*, vol. 40(8):1245–1254, (1993).

T. Aoki, *Chem. Abstr.*, vol. 113:84462q (1990).

(List continued on next page.)

*Primary Examiner*—Arlen Soderquist
*Attorney, Agent, or Firm*—Foley & Lardner

[57] ABSTRACT

To estimate nitric acid ions and nitrous acid ions in a sample solution, a method is proposed which comprises the steps of (a) feeding both the sample solution and a reducing agent to an acidic solution which is flowing in a thin pipe; (b) positively mixing the sample solution and the reducing agent and thus reacting the same in a given portion of the pipe; (c) leading the reacted solution to a gas/liquid separator thereby to separate a gaseous phase from the reacted solution; and (d) estimating the nitric acid ions and nitrous acid ions in the gaseous phase.

6 Claims, 12 Drawing Sheets

OTHER PUBLICATIONS

Hu et al., "Determination Of Ammonium Ion In Rainwater And Fogwater By Flow Injection Analysis With Chemiluminescence Detection", *Anal. Chem.,* vol. 65:3489–3492, (1993).

Sen et al., "Rapid And Sensitive Determination Of Nitrite In Foods And Biological Materials By Flow Injection Or High–Performance Liquid Chromatography With Chemiluminescence Detection", *Journal of Chromatography A,* vol. 673:77–84, (1994).

Dunham et al., "Aqueous Nitrite Ion Determination By Selective Reduction And Gas Phase Nitric Oxide Chemiluminescence", *Anal. Chem.,* vol. 67:220–224, (1995).

Patent Abstracts of Japan, vol. 14, No. 452, JP 02–181650, Sep. (1990).

Patent Abstracts of Japan, vol. 11, No. 283, JP 62–079364, Sep. (1987).

Patent Abstracts of Japan, vol. 4, No. 27, JP 55–001552, Mar. (1980).

J.G. Feinberg *Biochem. J.* 1976, 153, 721–723.

S. Katz et al. *J. Biochem. Biophys. Methods* 1980, 2, 63–70.

Aoki et al. *Anal. Chem.* 1983, 55, 209–212.

Aoki et al. *Environ. Sci. Technol.* 1986, 20, 515–517.

| | 14ppb | 140ppb |
|---|---|---|
| STANDARD DEVIATION | 0.089 | 0.167 |
| VARIATION COEFFICIENT | 3.719 | 1.699 |

NITROUS ACID IONS : 1.4ppm
NITRIC ACID IONS : 1.4ppm
POTASSIUM IODIDE : 10%
TITANIUM TRICHLORIDE : 20%

NITROUS ACID IONS : 1.4ppm
SULFURIC ACID : 1N

NITRIC ACID IONS : 1.4ppm
SULFURIC ACID : 1N

SULFURIC ACID : 1N

METHOD FOR ESTIMATING NITRIC ACID AND NITROUS ACID IONS

This application is a continuation of application Ser. No. 08/458,795, filed Jun. 2, 1995 now U.S. Pat. No. 5,668,014.

BACKGROUND OF THE INVENTION

1. Field of the Invention

The present invention relates in general to devices and methods for estimating the concentration of ionic substances in water, and more particularly, to devices and methods for estimating, with an aid of a flow-injection analyzing method, the concentration of ammonium ions ($NH_4^+$), nitric acid ions ($NO_3^-$) and nitrous acid ions ($NO_2^-$) which are the three nitrogen-containing ionic substances in water.

2. Description of the Prior Art

For estimating the concentration of the above-mentioned three nitrogen-including ionic substances in water, such as water of rivers, lakes and marshes, various methods have been proposed and put into practical use, which are for example, ion exchange chromatography method, calorimetric method, neutralization titration method and ion electrode method.

As is known, the ion exchange chromatography method is one of high speed liquid chromatography methods using an ion exchange column, which has been developed particularly for analyzing inorganic anions and cations. That is, the ion exchange chromatography method can precisely estimate the inorganic anions, such as $F^-$, $Cl^-$, $Br^-$, $NO_2^-$, $NO_3^-$, $SO_3^{2-}$, $SO_4^{2-}$ and $PO_{43}^-$. In this method, a column filled with anion exchange resin grains is used and a sample solution is led into the column from its top. With this, anions in the sample solution are adsorbed by the grains. Then, eluate containing a very small amount of competitive anion is led into the column. The amount of the competitive anion is so small that a conductivity meter can not detect it. Each anion adsorbed by the grains competes with the competitive anion and is eluted from the column with a certain mobility, so that the concentration of anion in the eluate can be estimated.

According to this ion exchange chromatography method, the ammonium ion can be estimated to a level of several ppm to several tens of ppm by using the conductivity meter. For the measurement, about ten minutes are usually needed from the time when the sample solution is led into the column. The quantitative concentration range of this method is relatively high, that is, from about 0.1 mg/l to about 30 mg/l.

Indophenol blue absorptiometric method is a typical one of the calorimetric methods. In this method, the indophenol blue which is produced when ammonium ion, with coexistence of hypochlorous acid ion, reacts with phenol is subjected to an absorbance test in which the absorbance of the light of 630 nm (nanometer) is measured. The quantitative concentration range of this method is relatively high, that is, from about 1.6 mg/l to about 33 mg/l.

In the neutralization titration method, ammonia, which has been extracted by effecting a distillation, is absorbed by a given amount of sulfuric acid (viz., 25 m mol/l) to prepare a sample solution, and the sample solution is subjected to a titration test using 50 m mol/l sodium hydroxide solution to estimate the ammonium ion. The quantitative concentration range of this method is relatively high, that is, from about 0.3 mg/l to about 40 mg/l.

In the ion electrode method, a sample, which has been subjected to a pretreatment, is added with sodium hydroxide solution to prepare a sample solution whose pH ranges from about 11 to about 13. With this process, ammonium ions are transformed to ammonia. By using an indicator electrode (viz., ammonia electrode), the potential of the sample solution to estimate the ammonium ions. The quantitative concentration range of this method is relatively high, that is, from about 0.1 mg/l to 100 mg/l.

As the calorimetric method, a so-called "sulfanilamide-naphthylethyldiamine method" and a so-called "phenoldisulfonic acid method" are also used. In the sulfanilamide-naphthylethyldiamine method, under acidity, sulfanilamide is led into water having nitrous acid ion. With this, the water becomes colored violet due to production of azo-coloring matter in the water. The colored water is then subjected to an absorptiometry to measure the absorbance of the color. With this, the concentration of nitrite nitrogen ($NO_2^-$—N) is determined. In the phenoldisulfonic acid method, sulfate is treated with phenoldisulfonic acid to produce nitrophenoldisulfornic acid solution which is colored yellow. The colored solution is then subjected to an absorptiometry to measure of the absorbance of the color. With this, the concentration of nitrate nitrogen ($NO_3^-$—N) is determined.

However, the above-mentioned methods have various drawbacks which are as follows.

That is, in case of the ion exchange chromatography method, a relative long measuring time (above ten minutes) is needed. Furthermore, as a pretreatment, filtering of the sample solution is needed for removing suspended solid and organic substances from the solution. Furthermore, water of rivers, lakes and marshes and sewage water can not be tested continuously because speedy treatment can not be made against contamination of them.

Usage of two types of ion exchange columns may be thought out. That is, one column is filled with cation exchange resin grains and the other column is filled with anion grains, and by switching the fluid passages to these two columns, cations and anions in a sample solution are estimated at the same time. However, this method brings about increase in number of movable portions of the equipment and thus increases the possibility of trouble. Furthermore, replacement of filters has to be made frequently for cleaning the sample solution.

In case of the calorimetric method, many manual labor operations are needed due to its inherence. Furthermore, a relatively large amount (viz., about 100 ml) of sample solution (viz., test water) is needed and about 30 to 60 minutes are needed for the measurement. Thus, automization of this method is very difficult. Furthermore, due to the inherence, this method is can not be used for measuring the concentration in ppb level.

In case of the neutralization titration method and the ion electrode method, troublesome operations are needed and relatively long time is needed for the measurement. Furthermore, the quantitative concentration range of these methods are relatively high, and thus, satisfied measurement has not been obtained in measuring efficiency and measuring accuracy.

SUMMARY OF THE INVENTION

It is therefore an object of the present invention to provide a method for estimating the concentration of ammonium ion ($NH_4^+$), nitric acid ion ($NO_3^-$) and nitrous acid ion ($NO_2^-$) which are the three nitrogen-containing ionic substances in water, the method being free of the above-mentioned drawbacks.

It is another object of the present invention to provide an analyzing device by which the method can be smoothly carried out.

According to a first aspect of the present invention, there is provided a method for estimating nitric acid ions and nitrous acid ions in a sample solution. The method comprises the steps of (a) feeding both the sample solution and a reducing agent to an acidic solution which is flowing in a thin pipe; (b) positively mixing the sample solution and the reducing agent and thus reacting the same in a given portion of the pipe; (c) leading the reacted solution to a gas/liquid separator thereby to separate a gaseous phase from the reacted solution; and (d) estimating the nitric acid ions and nitrous acid ions in the gaseous phase.

According to a second aspect of the present invention, there is provided an analyzing device for estimating nitric acid ions and nitrous acid ions in a sample solution. The analyzing device comprises a pipe; first means for feeding the pipe with a carrier; second means for feeding the pipe with the sample solution, a reducing agent and clean air; a mixing coil arranged in the pipe, the mixing coil positively mixing the sample solution and the reducing agent thereby producing a reacted solution; a gas/liquid separator arranged in the pipe downstream of the mixing coil, the separator separating a gaseous phase from the reacted solution; an ion detector arranged in the pipe downstream of the separator, the ion detector estimating the nitric acid ions and nitrous acid ions in the gaseous phase; and a recorder for recording the estimated results detected by the ion detector.

According to a third aspect of the present invention, there is provided a method for estimating ammonium ions, nitric acid ions and nitrous acid ions in a sample solution. The method comprises the steps of (a) feeding the sample solution to a carrier which is flowing in a thin pipe; (b) selectively feeding a plurality of reagents to the flowing carrier; (c) positively mixing the sample solution and the reagents one after another in a given portion of the pipe thereby producing three types of reacted solutions in the given portion; (d) leading the reacted solutions to a gas/liquid separator thereby to separate a gaseous phase from each reacted solution; (e) heating each gaseous phase to produce nitrogen monoxide; and (f) estimating the ammonia ions, the nitric acid ions and the nitrous acid ions in the three types of nitrogen monoxides produced.

According a fourth aspect of the present invention, there is provided an analyzing device for estimating ammonium ions, nitric acid ions and nitrous acid ions in a sample solution. The analyzing device comprises a pipe; means for feeding the pipe with a carrier; first means for feeding the carrier with the sample solution; second means for selectively feeding a plurality of reagents to the flowing carrier; a mixing coil arranged in the pipe, the mixing coil positively mixing the sample solution the reagents one after another thereby to produce three types of reacted solutions; a gas/liquid separator arranged in the pipe downstream of the mixing coil, the separator separating a gaseous phase from each-reacted solution; a heater for heating each gaseous phase thereby to produce nitrogen monoxide; and a detector for estimating the ammonia ions, the nitric acid ions and the nitrous acid ions in the three types of nitrogen monoxides produced.

BRIEF DESCRIPTION OF THE DRAWINGS

Other objects and advantages of the present invention will become apparent from the following description when taken in conjunction with the accompanying drawings, in which.

DETAILED DESCRIPTION OF THE EMBODIMENTS

In the following, various embodiments of the present invention will be described in detail with reference to the accompanying drawings.

As is become apparent as the description proceeds, the present invention is based on a so-called "flow-injection analyzing method" developed in 1975 in Denmark by Ruzicka and Hansen and aims to estimate or measure the quantity of ammonium ion ($NH_4^+$), nitric acid ion ($NO_3^-$) and nitrous acid ion ($NO_2^-$) in water.

In the flow-injection analyzing method, a sample solution and a reagent are continuously injected into a carrier which flows continuously. The sample solution and the reagent are reacted in a mixing coil. The reaction product thus produced in the mixing coil is estimated by various detectors.

Figure 1:
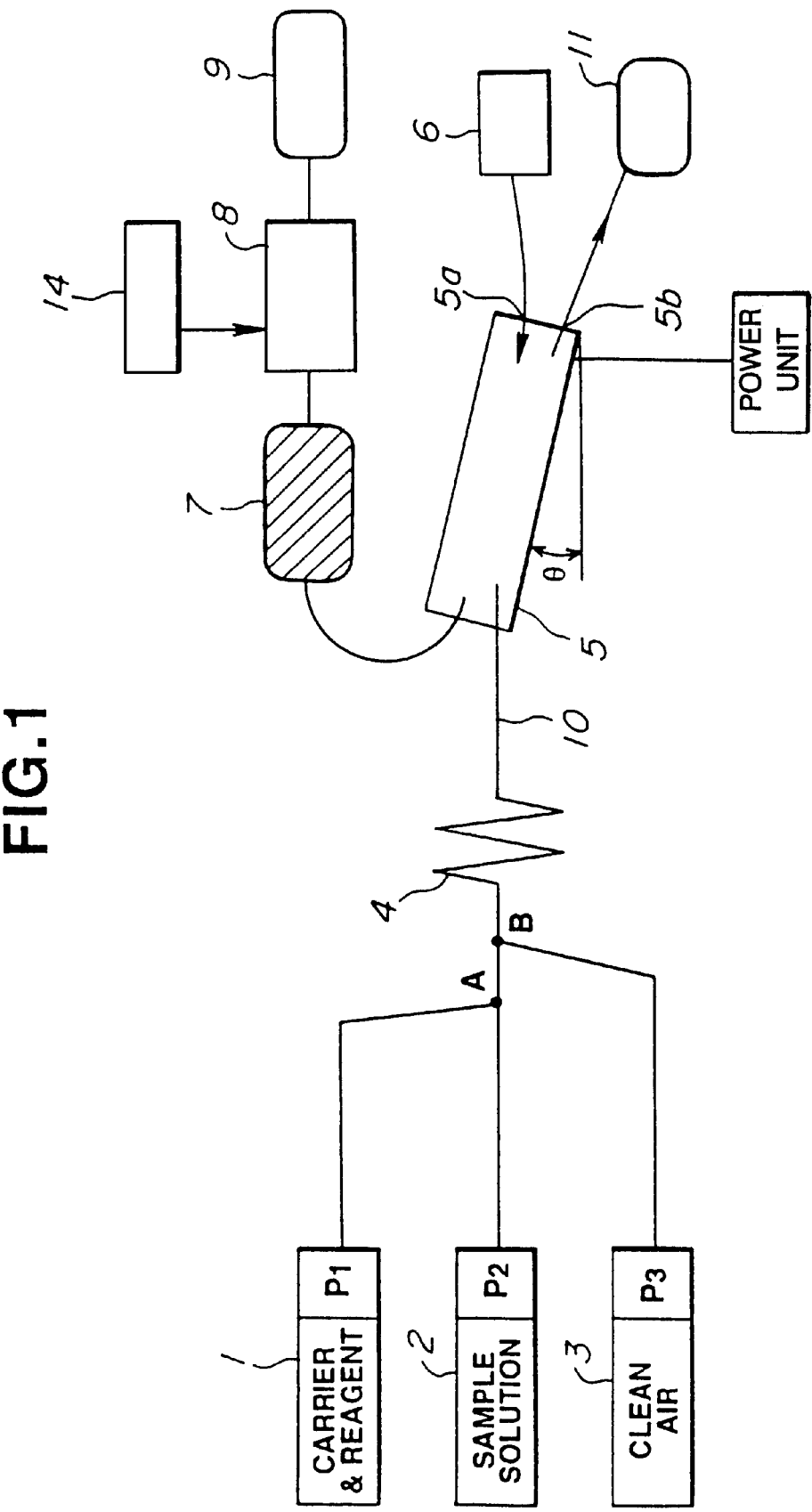
FIG. 1 is a schematic view of an analyzing device for estimating ammonium ion, which is a first embodiment of the present invention.

Referring to FIG. 1, there is schematically shown an analyzing device by which a method for estimating ammonium ions in test water is carried out, the method being a first embodiment of the present invention.

In the drawing, denoted by numeral 1 is an inlet opening for both a carrier and a reagent, 2 is an inlet opening for a sample solution and 3 is an inlet opening for clean air. In this first embodiment, as a reagent led into the carrier inlet opening 1, hypochlorous acid (HOCl) or sodium hypochlorite (NaClO) is used.

Designated by references $P_1$, $P_2$ and $P_3$ are pumps, 4 is a mixing coil and 5 is a gas/liquid separator. The separator 5 is provided with a clean air inlet opening 5a and a waste liquid outlet opening 5b. The separator 5 comprises a glass tube in which a gas permeable membrane is arranged. As shown, the separator 5 is inclined at a given degree "θ" relative to the horizontal surface. The separator 5 is rotated about its axis by a power unit (not shown).

Designated by numeral 6 is a source of clean air, 7 is a heating furnace, 8 is a detector, 14 is an ozonizer and 9 is a recorder. In the first embodiment, as the detector 8, a chemiluminescent detector is used. The parts are connected by a thin pipe 10 in the illustrated manner. The thin pipe 10 is constructed of Teflon (trade name) whose inner diameter is about 0.5 mm to 1.0 mm.

By the mixing coil 4, there is produced a turbulent flow by which a mixing and thus a reaction between the sample solution and the reagent is smoothly carried out. In fact, the mixing coil 4 is a coiled thin tube of Teflon (trade name). The diameter of the tube is about 0.5 mm to 1.0 mm. The length of the coil is determined in accordance with the mixing ability which is required by a user.

For obtaining a desired repeatability, a rotary valve type injector (not shown) is used to feed the sample solution into the inlet opening 2. As the pumps $P_1$, $P_2$ and $P_3$, BERRY-STAR TYPE pumps are used, each having a pumping capacity of about 0.1 to several ml/min.

In the following, a process for estimating ammonium ions in a test water by using the above-mentioned flow-injection analyzing device of FIG. 1 will be described, which is the first embodiment of the present invention.

Under operation of the pump $P_2$, the test water containing the ammonium ions is led into the sample solution inlet opening 2, and under operation of the pump $P_1$, hypochlorous acid (HOCl) (or sodium hypochlorite (NaClO)) is led into the reagent inlet opening 1. With this, they are mixed at point "A" of the pipe 10. For increasing the mixed condition of them at point "B", clean air is led into the clean air inlet opening 3 under operation of the pump $P_3$.

The ammonium ions and the hypochlorous acid are thus mixed sufficiently in the mixing coil 4 and reacted and then led into the gas/liquid separator 5. Due to feeding of clean air into the separator 5 from the clean air source 6, the gas separation from the liquid phase in the mixing coil 4 is promoted. The gaseous components from the separator 5 are led into the heating furnace 7, while a waste liquid from the waste liquid outlet opening 5b of the separator 5 is led to a waste liquid tank 11.

When heated by the heating furnace 7, the gaseous components are transformed into nitrogen monoxide (NO), and the sample gas thus containing the nitrogen monoxide (NO) is led into the detector 8 into which ozone gas from the ozonizer 14 is being fed. Thus, the nitrogen monoxide (NO) in the sample gas is reacted with the ozone gas ($O_3$) to produce a chemiluminescence whose intensity is detected by the detector 8. With this, the concentration of the nitrogen monoxide (NO) in the sample gas is measured and recorded by the recorder 9.

By using the above-mentioned process, many tests were carried out by the inventors and the results of them are depicted in FIGS. 2 to 5.

Figure 2:
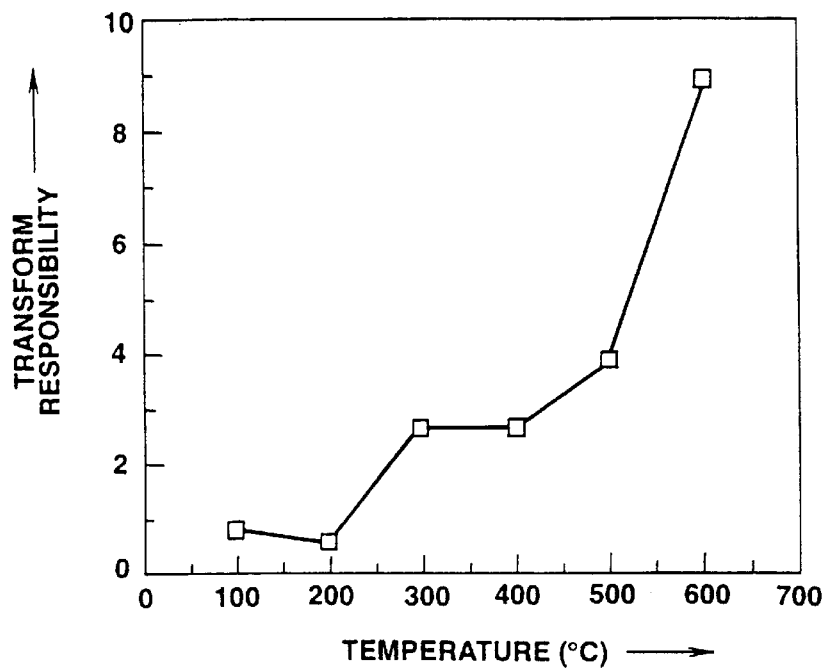
FIG. 2 is a graph showing a relationship between the temperature of a heating furnace installed in the analyzing device of the first embodiment and the transform-responsibility with which gaseous components are transformed into nitrogen monoxide.

FIG. 2 is a graph showing the relationship between the temperature of the heating furnace 7 and the transform-responsibility with which the gaseous components are transformed into nitrogen monoxide (NO). As is understood from this graph, the transform-responsibility showed a sufficient value at about 600° C.

Figure 3:
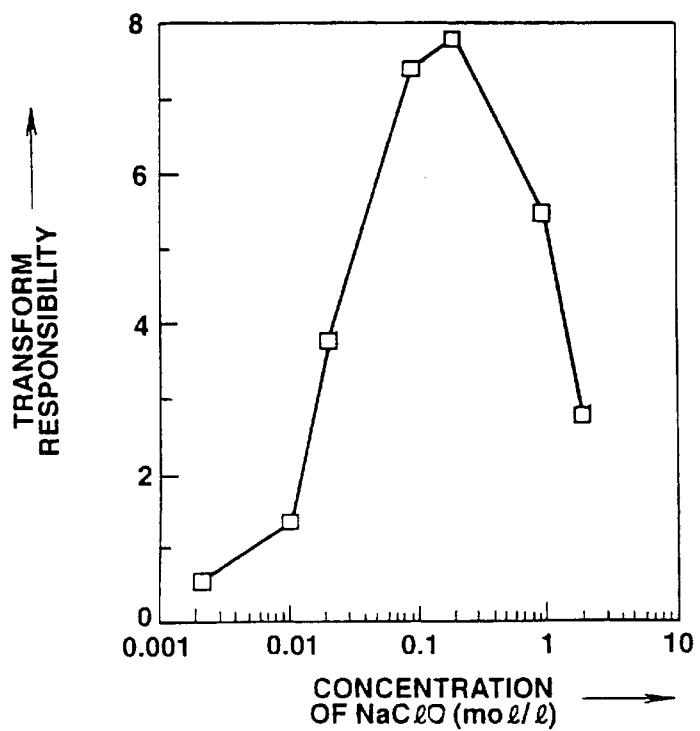
FIG. 3 is a graph showing a relationship between the concentration of sodium hypochloride (reagent) and the transform-responsibility.

FIG. 3 is a graph showing a relationship between the concentration (mol/l) of sodium hypochlorite (NaClO,pH7) and the transport-responsibility. As is known, the sodium hypochlorite (NaClO) is a reagent for reducing ammonium ions in water to nitrogen monoxide (NO). As is understood from this graph, the transform-responsibility showed the maximum value at about 0.02 (mol/l) concentration of the sodium hypochlorite. In case of hypochlorous acid (HOCl) as the reagent, substantially the same result was obtained.

Figure 4:
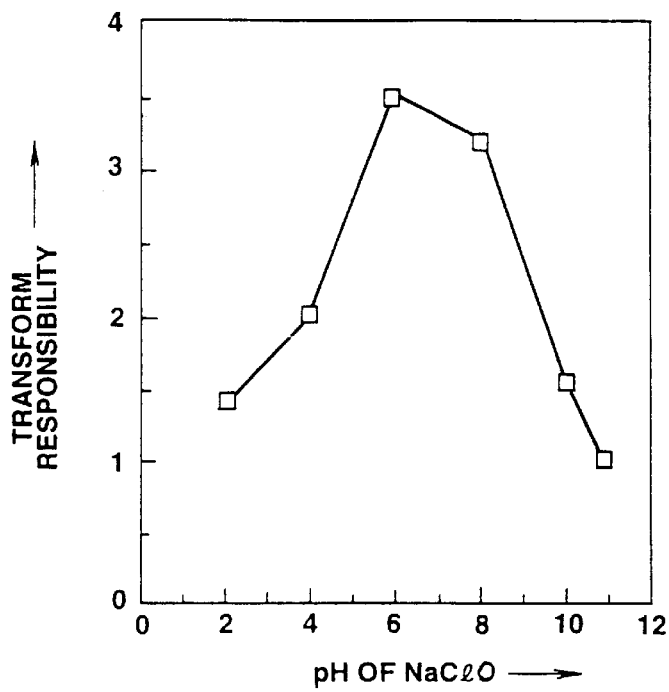
FIG. 4 is a graph showing a relationship between "pH" of sodium hypochloride and the transform-responsibility.

FIG. 4 is a graph showing a relationship between "pH" of sodium hypochloride (NaClO) and the transform-responsibility, from which the "pH" dependency of the sodium hypochloride with respect to the transform-responsibility is known. As is understood from this graph, the transform-responsibility showed the maximum value at about pH5 to pH8 (viz., near neutral).

Figure 5:
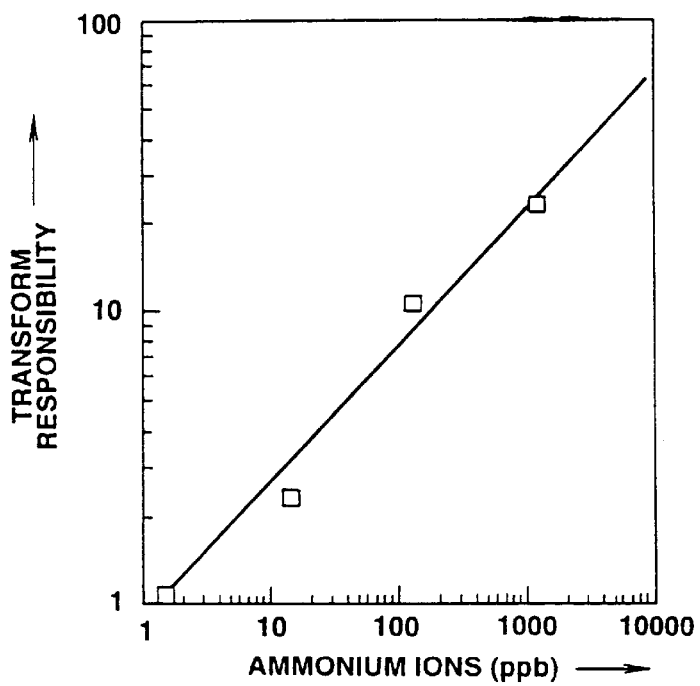
FIG. 5 is a graph showing the analytical curve of ammonium ion.

Considering this result, for providing the analytical curve of ammonium ions, tests were carried out under a condition wherein the concentration of the sodium hypochlorite (NaClO) was 0.02(mol/1) and the "pH" of the same was about 5 to 8. The curve is shown by the graph of FIG. 5. As is seen from this graph, the analytical curve showed a desired linearity (or desired transform-responsibility) at a relatively low concentration range, that is, from 1 ppb (=µg/l) to 1500 ppb (=1.5 mg/l) of the ammonium ions. Furthermore, the analytical curve had a satisfaction in the standard deviation and the variation coefficient.

Figure 6:
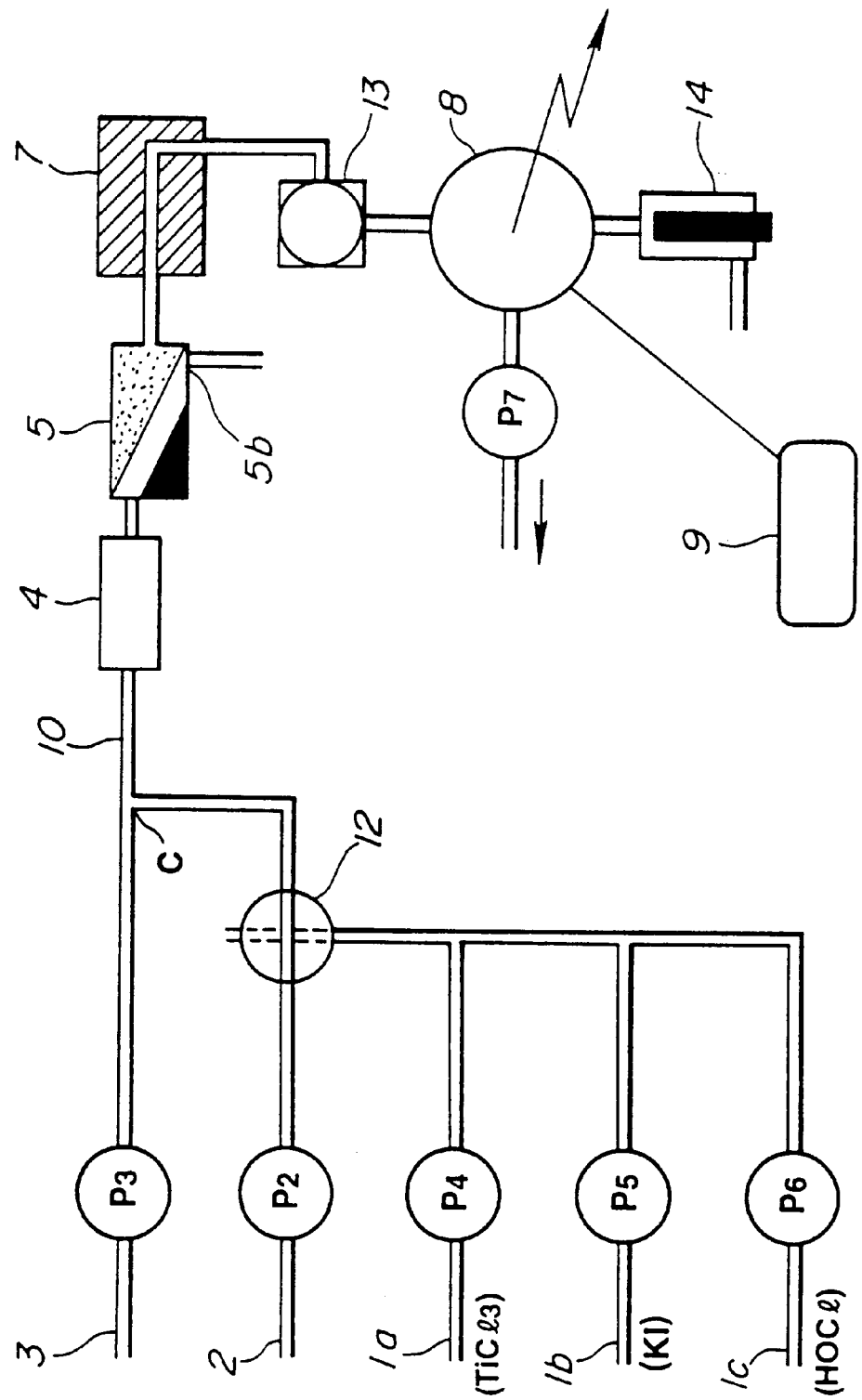
FIG. 6 is a schematic view of an analyzing device for estimating the three nitrogen-including ionic substances in water, which is a second embodiment of the present invention.

Referring to FIG. 6, there is schematically shown an analyzing device by which a method for estimating the three nitrogen-including ionic substances in water is carried out, the method being a second embodiment of the present invention. As has been mentioned hereinabove, the three nitrogen-including ionic substances in water are ammonium ion ($NH_4^+$), nitric acid ion ($NO_3^-$) and nitrous acid ion ($NO_2^-$).

In FIG. 6, for ease of understanding, parts or portions similar to those of the above-mentioned first embodiment (FIG. 1) are denoted by the same reference numerals.

In the drawing, denoted by references, 1b and 1c are inlet openings for both the carrier and the reagents, 2 is an inlet opening for a sample solution and 3 is an inlet opening for clean air. In this second embodiment, as a reagent led into the first reagent inlet opening 1a, titanium trichloride ($TiCl_3$) is used, as a reagent led into the second reagent inlet opening 1b, potassium iodide (KI) is used, and as a reagent led into the third reagent inlet opening 1c, hypochlorous acid (HOCl) is used.

Designated by references $P_2$ to $P_7$ are pumps, and 12 is a mixing valve for each reagent. Designated by numeral 10 is a pipe for connecting the various parts in the illustrated manner. 4 is a mixing coil, 5 is a gas/liquid separator, 7 is a heating furnace, 13 is a dryer, 8 is a detector, 9 is a recorder and 14 is an ozonizer. As the detector 8, a reduced pressure type chemiluminescent detector is used.

In the following, a process for estimating the three nitrogen-including ionic substances in a test water by using the analyzing device of FIG. 6 will be described, which is the second embodiment of the present invention.

First, a process for estimation of nitric acid ion ($NO_3^-$) will be described.

Under operation of the pump $P_2$, the test water containing nitric acid ions is led into the sample solution inlet opening 2, and under operation of the pump $P_4$, titanium trichloride ($TiCl_3$) as a reagent is led into the first reagent inlet opening 1a. Then, the mixing valve 12 is manipulated to mix them. Then, under operation of the pump $P_3$, clean air is fed into the clean air inlet opening 3, the mixed components meet the clean air at point "C" and they are led to the mixing coil 4. The test water and the reagent are thus mixed sufficiently in the mixing coil 4 to achieve a sufficient reaction therebetween. Then, they are led into the gas/liquid separator 5. The gaseous components from the separator 5 are led into the heating furnace 7, while a waste liquid from the separator 5 is discharged through the outlet opening 5b.

When heated at about 600° C., the gaseous components are transformed into nitrogen monoxide (NO), and the sample gas thus produced is led into the dryer 13 and then led to the detector 8 under operation of the pump $P_7$. The nitrogen monoxide (NO) in the gaseous phase is reacted with the ozone gas ($O_3$) to produce a chemiluminescence whose intensity is detected by the detector 8 and recorded by the recorder 9.

The chemi-luminescence detector 8 is of a NOx type which can measure nitrogen oxides. The chemi-luminesecence is the luminous phenomenon which occurs when excited molecules are returned to the ground state. By analyzing the emission spectrum, a qualitative analysis of the sample is achieved, and by measuring the luminous energy, a quantitative analysis is achieved. That is, the chemi-luminescence detector 8 used in this embodiment is of a type which practically uses the fact wherein the intensity of the chemi-luminescence produced from the reaction between NO in the sample gas and $O_3$ is substantially proportional to the concentration of NO. Thus, the concentration of the nitrogen monoxide (NO) in the sample gas is measured for estimating the nitric acid ion ($NO_3^-$) in water.

Now, a process for estimation of nitrous acid ion ($NO_2^-$) will be described.

Similar to the above case, under operation of the pump $P_2$, the test water containing nitrous acid ions is led into the sample solution inlet opening 2, and under operation of the pump $P_5$, potassium iodide (KI) as a reagent is led into the second reagent inlet opening 1b. Then, the mixing valve 12 is manipulated to mix them. Then, under operation of the pump $P_3$, clean air is fed into the clean air inlet opening 3, the mixed components meet the clean air at point "C" and they are led to the mixing coil 4 and reacted there. Then, they are led into the gas/liquid separator 5. The gaseous components from the separator 5 are led into the heating furnace 7, while a waste liquid from the separator 5 is discharged through the outlet opening 5b.

Thereafter, like in the case of the above-mentioned nitric acid ions, a chemiluminescence produced by the reaction between the nitrogen monoxide (NO) in the gaseous phase and the ozone gas ($O_3$) from the ozonizer 14 is measured by the detector 8 and recorded by the recorder 9.

As is understood from the above, in the second embodiment, a reagent is fed to a test water to reduce nitric acid ions ($NO_3^-$) or nitrous acid ions ($NO_2^-$) to nitrogen monoxide (NO) and the nitrogen monoxide is reacted with ozone gas ($O_3$). That is, since the detector 8 is of the chemi-luminescent detector which is designed to measure the intensity of the luminescence produced when NO and $O_3$ are reacted, such reduction is necessary for estimating the nitric acid ions ($NO_3^-$) or nitrous acid ions ($NO_2^-$) to nitrogen monoxide (NO).

The nitric acid ion ($NO_3^-$) has three oxygen atoms while the nitrous acid ion ($NO_2^-$) has two oxygen atoms. Thus, the nitrous acid ion ($NO_2^-$) is easily reduced to the nitrogen monoxide (NO) as compared with the nitric acid ion ($NO_3^-$). By using this difference, in the second embodiment, two reducing agents are employed, one being the potassium iodide (KI) which can reduce the nitrous acid ion ($NO_2^-$) only, and the other being the titanium trichloride ($TiCl_3$) which can reduce both the nitrous acid ions ($NO_2^-$) and the nitric acid ions ($NO_3^-$). The reaction formulas of them are shown in the following.

$$NO_3^- + 3Ti^{3+} \rightarrow NO + 3Ti^{4+} \quad (1)$$

$$2NO_2^- + 2I^- \rightarrow 2NO + I_2 \quad (2)$$

While, in case of estimating ammonium ion ($NH_4^+$), the test water containing ammonium ions is led into the sample solution inlet opening 2, and under operation of the pump $P_6$, hypochlorous acid (HOCl) is led into the third reagent inlet opening 1c. Thereafter, similar operations are carried out. With this, the ammonium ions are transformed into the nitrogen monoxide (NO) which is thereafter subjected to the chemi-luminescence analysis as mentioned hereinabove.

Although, in the above description in the second embodiment, the process for estimating the three nitrogen-including ionic substances (viz., $NH_4^+$, $NO_3^-$ and $NO_2^-$) is explained separately, these three substances can be continuously estimated or measured. For this continuous measurement, the three reagents (viz., titanium trichloride, potassium iodide and hypochlorous acid) are intermittently fed to a sample solution which continuously flows in the tube 10. In this case, the detector 8 issues continuously three types of outputs, one being an output proportional to the concentration of nitrous acid, one being an output proportional to the concentration of nitrous acid and nitric acid and the other being an output proportional to the concentration of ammonia.

Figure 7:
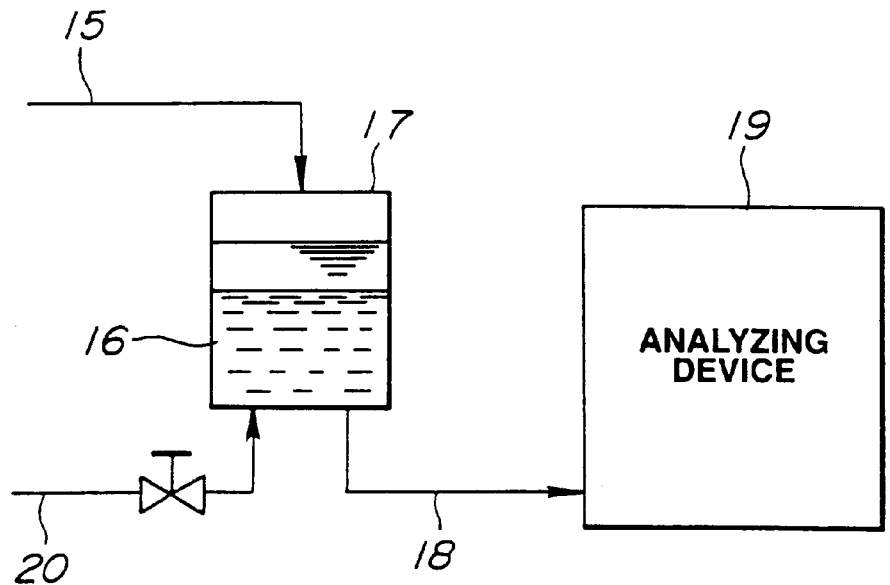
FIG. 7 is a schematic view showing a first modification of the analyzing device of the second embodiment.

FIG. 7 shows a first modification of the above-mentioned second embodiment.

In this modification, a filter 17 is further employed, which cleans the test water 15 before the latter is subjected to the substance estimating process. A filter medium 16 is packed in the filter 17. For cleaning the filter medium 16, a clean water pipe 20 is connected to the bottom of the filter 17. Filtered water from the filter 17 is led to the analyzing device 19 through a pipe 18. In fact, this modification is very useful to examine water which is contaminated with suspended solids.

Figure 8:
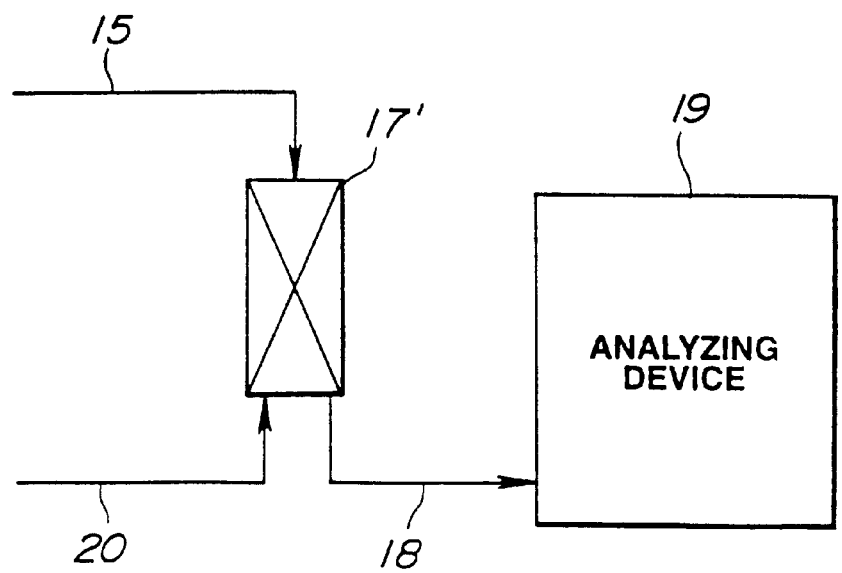
FIG. 8 is a view similar to FIG. 7, but showing a second modification of the analyzing device of the second embodiment.

FIG. 8 shows a second modification of the second embodiment. In this modification, a ultrafiltration film or hollow fiber is used as the filter medium of the filter 17'.

Figure 9:
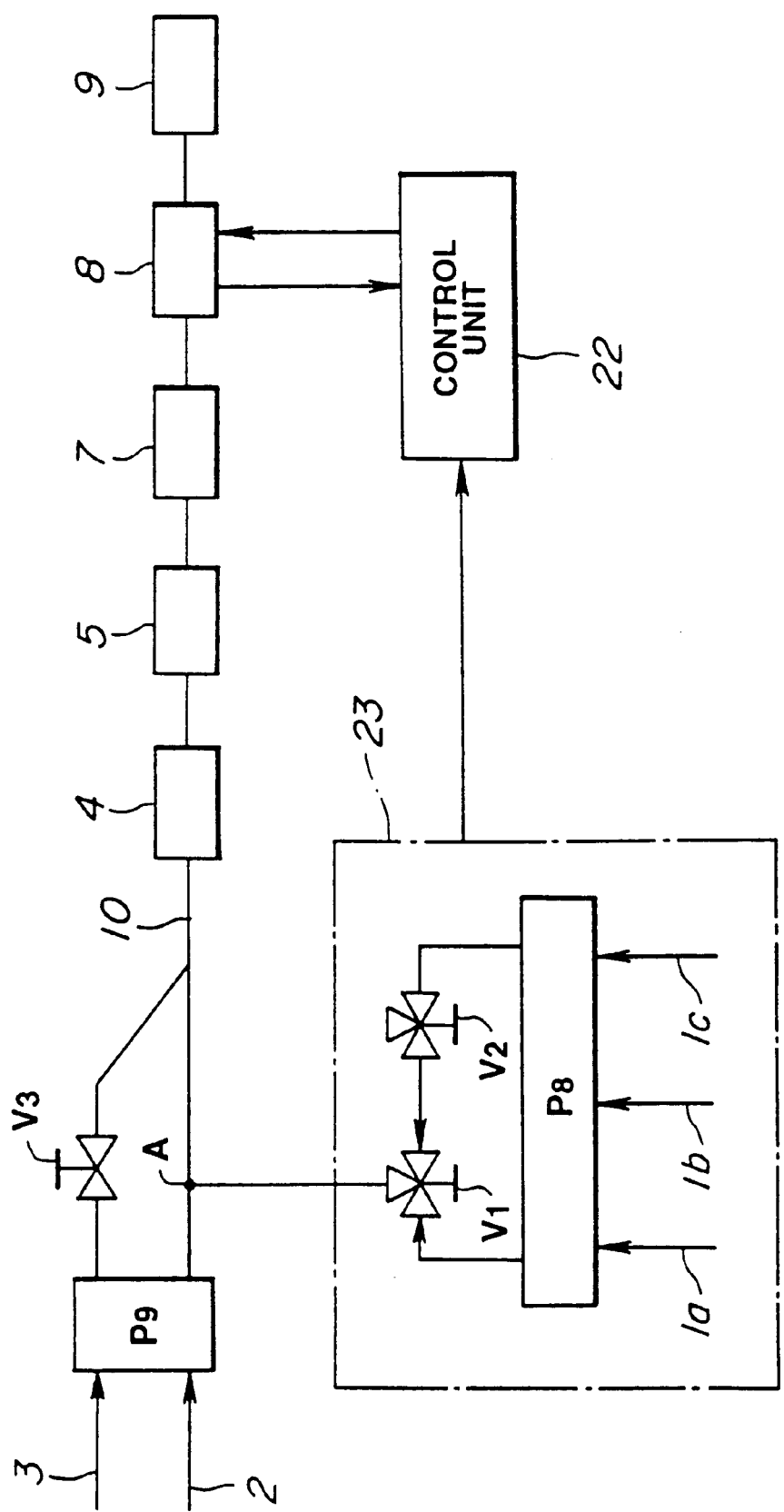
FIG. 9 is a schematic view of an automized analyzing system for automatically estimating the three-nitrogen including ionic substances in water, which is a third embodiment of the present invention.

Referring to FIG. 9, there is shown an automized analyzing system which can automatically estimate the three-nitrogen including ionic substances in water, the system being a third embodiment of the present invention. For ease of understanding, parts or portions similar to those of the above-mentioned first and second embodiments (FIGS. 1 and 6) are denoted by the same reference numerals.

In the system of this third embodiment, near the inlet opening "A" of the pipe 10 for the reagent, there are arranged three tanks (not shown) for hypochlorous acid (HOCl) (or sodium hypochlorite (NaClO)), titanium trichloride (TiCl$_3$) and potassium iodide (KI). From the tanks, there extend respective feeding pipes 1a, 1b and 1c which are connected to the inlet opening "A" of the pipe 10 through a reagent feeding mechanism 23 which comprises a pump P$_8$ and two electromagnetic valves V$_1$ and V$_2$. The valves V$_1$ and V$_2$ are used for selectively feeding the three reagents to the pipe 10. Designated by numeral 22 is a control unit which is interposed between the reagent feeding mechanism 23 and the detector 8.

In operation of the automized analyzing system, under operation of the pump P$_9$, test water is fed to the pipe 10 from the sample solution inlet opening 2 and at the same time clear air is fed to the pipe 10 from the clean air inlet opening 3 while adjusting an adjusting valve V$_3$. Thereafter, under operation of the pump P$_8$, ON-OFF operation of the two valves V$_1$ and V$_2$ is selectively carried out so as to feed the three reagents (viz., titanium trichloride (TiCl$_3$), potassium iodide (KI) and hypochlorous acid (HOCl)) to the pipe 10 independently one after another.

Like the above-mentioned cases, the test water and the reagent solution are mixed at the mixing coil 4, and then they are led to the gas/liquid separator 5. The gas components from the separator 5 are led to the heating furnace 7 and transformed into nitrogen monoxide (NO). The nitrogen monoxide (NO) is thereafter subjected to the chemi-luminescence analysis in such a manner as has been mentioned hereinafore. By analyzing information signals from the reagent feeding mechanism 23 and the detector 8, the control unit 22 calculates the sum of the three nitrogen-including ionic substances based on the analytic curves provided by them.

Figure 10:
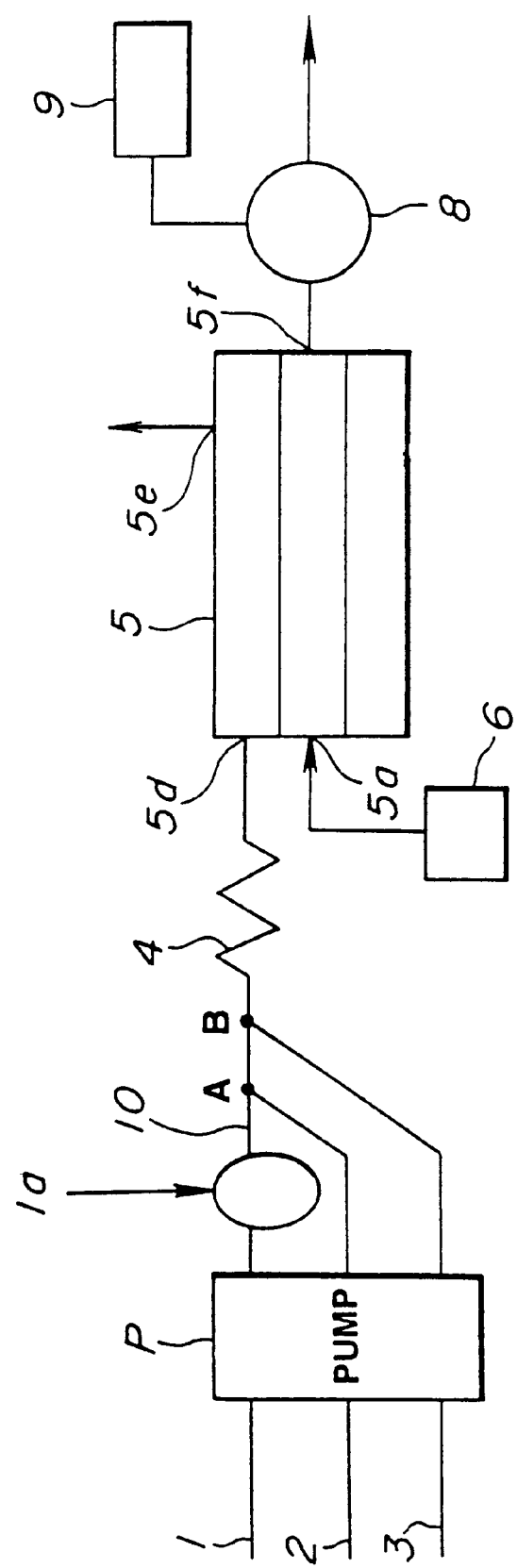
FIG. 10 is a schematic view of an analyzing device for estimating nitric acid ions and nitrous acid ions in test water, which is a fourth embodiment of the present invention.

Referring to FIG. 10, there is schematically shown an analyzing device by which a method for estimating nitric acid ion (NO$_3^-$) and nitrous acid ion (NO$_2^-$) in test water is carried out, the method being a fourth embodiment of the present invention.

In the drawing, denoted by reference P is a pump, 1 is an inlet opening for a carrier, 2 is an inlet opening for a sample solution and 3 is an inlet opening for clean air. In this fourth embodiment, as the carrier led into the carrier inlet opening 1, 1N-sulfuric acid is used. For smoothly feeding the sample solution into the sample solution inlet opening 2, a rotary valve type injector is used. The injection rate is from about 10 $\mu$l to about 100 $\mu$l. As the pump P, a BERRY-STAR TYPE pump is used whose pumping capacity is about 0.1 to several ml/min.

Designated by reference 1a is an inlet opening for a reagent, 4 is a mixing coil and 5 is a membrane type separator. The separator 5 is provided with a clean air inlet opening 5a through which clean air from a clean air source 6 is led into the separator 5. The mixing coil 4 is a coiled thin tube of Teflon (trade name) whose diameter is about 1.0 mm and whose length is about 200 cm.

Denoted by numeral 8 is a detector, that is, a chemi-luminescence detector and 9 is a recorder. These parts are connected by a pipe 10 which is constructed of Teflon (trade name). Preferably, the inner diameter of the pipe 10 is about 0.5 mm to 1.0 mm.

Figure 11:
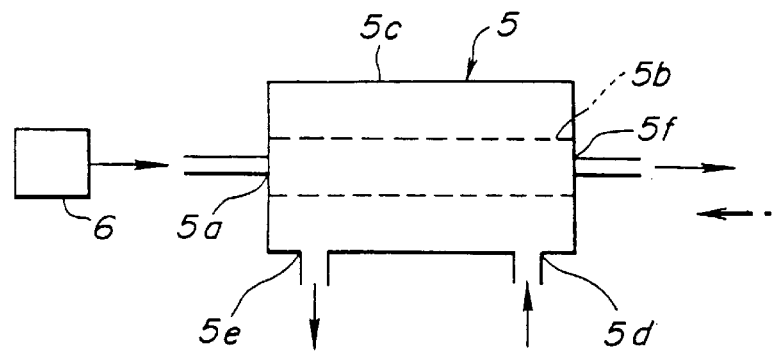
FIG. 11 is a schematic view of a membrane type separator installed in the analyzing device of the fourth embodiment.
Figure 12:
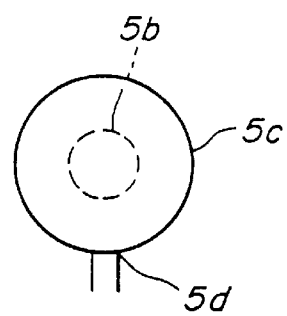
FIG. 12 is a schematic view taken from the direction of the arrow "XII" of FIG. 11.

As is seen from FIGS. 11 and 12, the membrane type separator 5 comprises inner and outer cylinders 5b and 5c which are coaxially arranged. The inner cylinder 5b is a perforated tube of Teflon (trade name) whose inner diameter is 2 mm and whose length is 20 cm. While, the outer cylinder 5c is a nonpermeable tube of Teflon (trade name) whose inner diameter is 4 mm and whose length is 20 cm. The clean air inlet opening 5a is connected to the interior of the inner cylinder 5b. The outer cylinder 5c is equipped with both an inlet opening 5d into which the mixed and reacted solution from the mixing coil 4 is led and a waste discharge opening 5e from which a waste liquid separated from the mixed and reacted solution is discharged.

The chemi-luminescence detector 8 is of a NOx type which can measure nitrogen oxides. More specifically, the detector 8 employed in the fourth embodiment is the "238-type" detector produced in KIMOTO DENSHI CO., LTD.

In the following, a process for estimating the nitric acid ions (or nitrous acid ions) in a test water by using the analyzing device of FIG. 10 will be described.

Under operation of the pump P, an acidic solution including 1N-sulfuric acid (carrier) is led into the carrier inlet opening 1. With the acidic solution being led into the opening 1, a test water is led into the sample solution inlet opening 2, and at the same time, a reducer of 100 $\mu$l of titanium trichloride (or 100 $\mu$l of potassium iodide in case of nitrous acid ions) is led into the reagent inlet opening 1a. With this, the test water and the reducer meet at the point "A" and then sufficiently mixed at the mixing coil 4 and reacted. For promoting the mixing and thus reaction of them, clean air is led into the point "B" from the clean air inlet opening 3.

Then, the reacted solution from the mixing coil 4 is led into the membrane type separator 5 through the inlet opening 5d. In the separator 5, nitrogen monoxide (NO) is separated from the reacted solution and led into the detector 8 together with the clean air from the clean air source 6. The waste liquid from the separator 5 is discharged to a waste liquid tank (not shown) through the waste discharge opening 5e.

The intensity of the chemiluminescence, which has been produced by the reaction between nitrogen monoxide (NO) in the gaseous phase and ozone gas (O$_3$), is detected by the detector 8 and recorded by the recorder 9.

Figure 13:
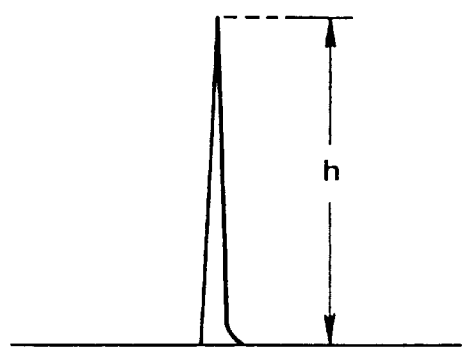
FIG. 13 is a graph showing a typical signal pattern of chemiluminescence recorded by a recorder when a test water is tested by the analyzing device of the fourth embodiment.

FIG. 13 shows a typical signal pattern recorded by the recorder 9. By measuring the height "h" of the pattern, the concentration of "NOx" is known.

In this fourth embodiment, the following reduction reactions are carried out like in the above-mentioned second embodiment.

That is:

$$NO_3^- + 3Ti^{3+} \rightarrow NO + 3Ti^{4+} \qquad (1)$$

$$2NO_2^- + 2I^- \rightarrow 2NO + I_2 \qquad (2)$$

These reduction reactions show a higher reaction efficiency under acidic condition, and the titanium trichloride tends to produce precipitates under a condition other than the acidic condition. The precipitates may lower the performance of the membrane type separator 5. Accordingly, 1N-sulfuric acid is used as the carrier. If, in place of sulfuric acid, hydrochloric acid or nitric acid is used as the carrier, sufficient intensity detection for chemiluminescence can not be expected by the detector 8 because they may permeate the membrane type separator 5. Phosphoric acid can not be used as the carrier because it produces insoluble materials with titanium trichloride.

By using the above-mentioned process, many tests were carried out by the inventors and the results of them are depicted FIGS. 14 to 19.

Figure 14:
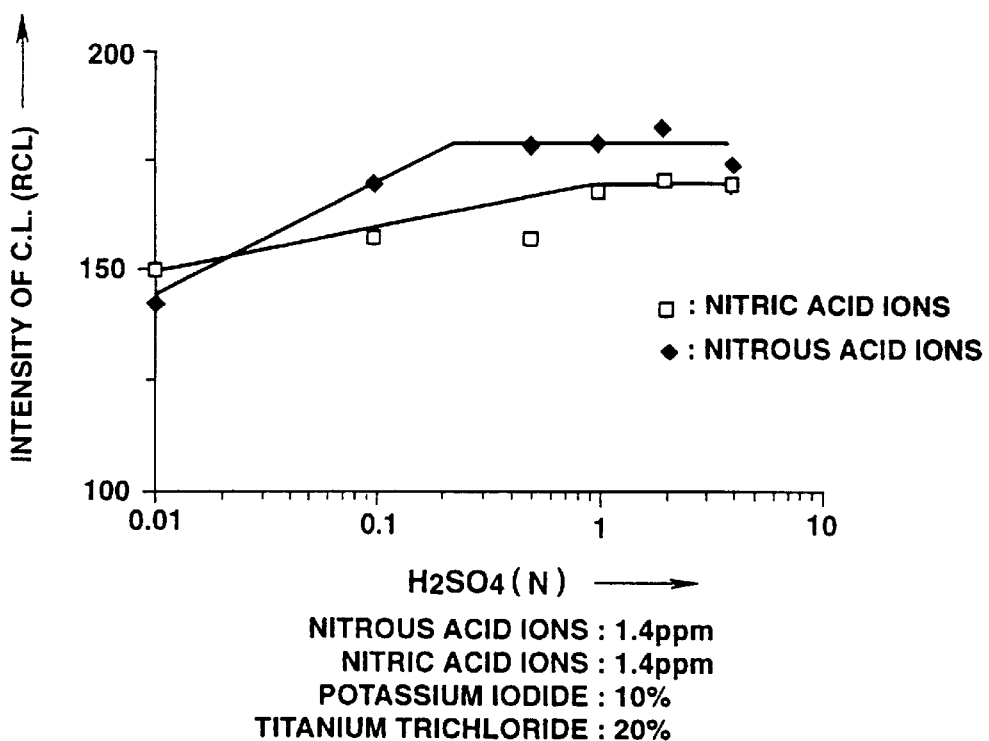
FIG. 14 is a graph showing a relationship between the concentration (N) of sulfuric acid and the intensity (RCL) of chemiluminescence.

FIG. 14 is a graph showing a relationship between the concentration (N) of sulfuric acid (carrier) and the intensity (RCL) of the produced chemiluminescence. The concentration of nitrous acid ions or nitric acid ions in the test water was 1.4 ppm and the concentration of potassium iodide was 10% and the concentration of titanium trichloride was 20%. 1N-sulfuric acid was used as the carrier. It was found that if the concentration of sulfuric acid was lower than 1N, the reduction efficiency was lowered.

Figure 15:
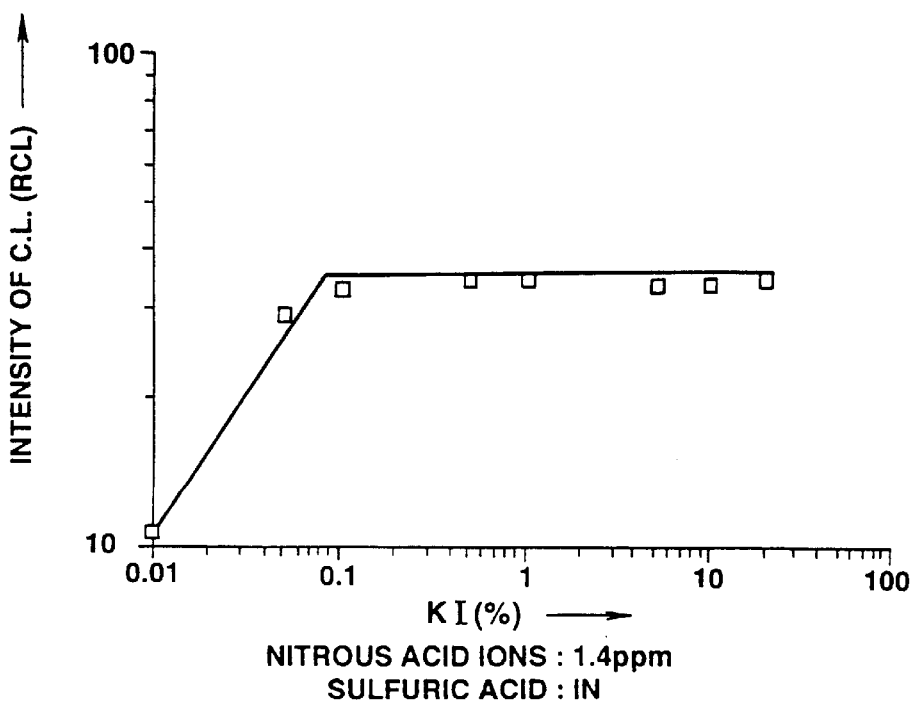
FIG. 15 is a graph showing a relationship between the concentration (%) of potassium iodide and the intensity (RCL) of chemiluminescence.

FIG. 15 is a graph showing a relationship between the concentration (%) of potassium iodide and the intensity (RCL) of the produced chemiluminescence. As is seen from this graph, when the concentration of potassium iodide was from 0.1% to 20%, a constant intensity of chemiluminescence was obtained. About 10% is preferable.

Figure 16:
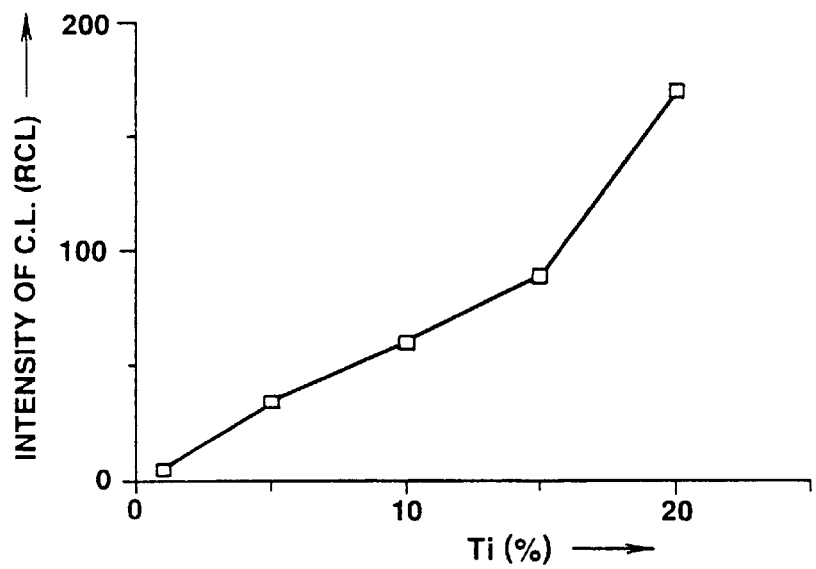
FIG. 16 is a graph showing a relationship between the concentration (%) of titanium trichloride and the intensity (RCL) of chemiluminescence.

FIG. 16 is a graph showing a relationship between the concentration (%) of titanium trichloride and the intensity (RCL) of the produced chemiluminescence. As is seen from the graph, the intensity increased with increase of the concentration of titanium trichloride. As is understood from the graph, when the concentration of titanium trichloride solution is greater than 5%, satisfactory intensity of chemiluminescence is produced. Preferably, the concentration is about 20%.

Figure 17:
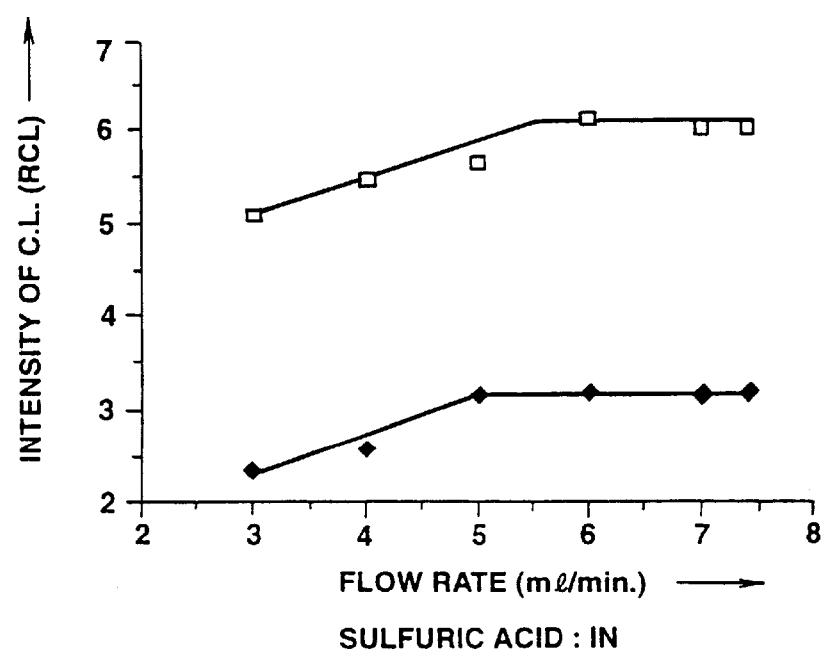
FIG. 17 is a graph showing a relationship between the flow rate of clean air for bubbling and the intensity (RCL) of chemiluminescence.

FIG. 17 is a graph showing a relationship between the flow rate of clean air fed to the clean air inlet opening 3 (see FIG. 10) and the intensity (RCL) of the produced chemiluminescence. As is seen from the graph, about 6 ml/min is preferable in the flow rate.

Figure 18:
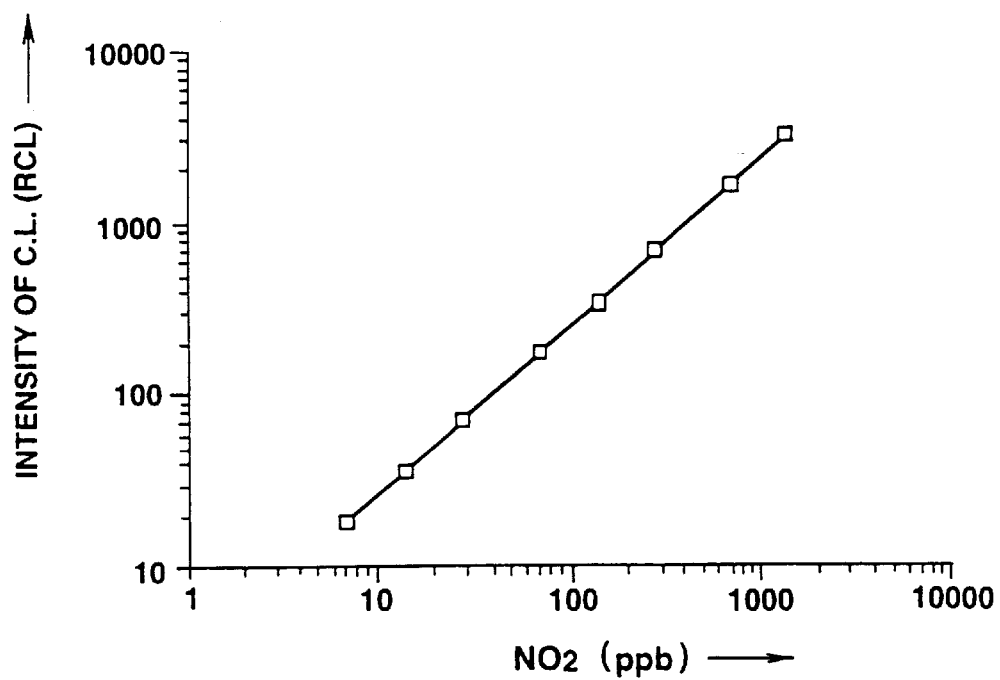
FIG. 18 is a graph showing the analytical curve of nitrous acid ion and potassium iodide.
Figure 19:
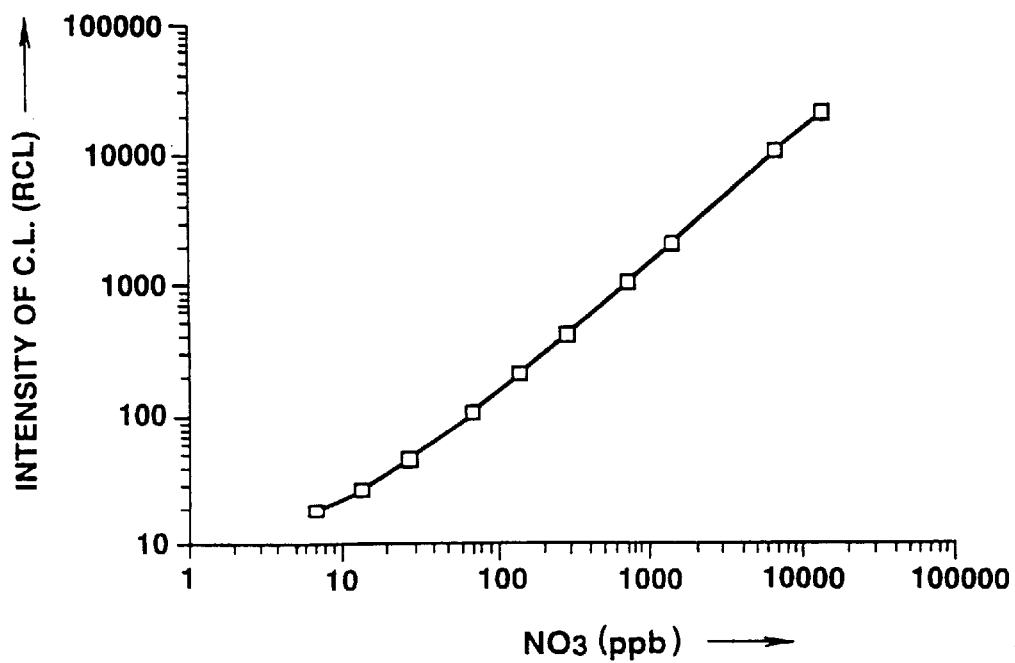
FIG. 19 is a graph showing the analytical curve of nitric acid ion and titanium trichloride.

FIG. 18 is a graph showing the analytical curve of nitrous acid ions ($NO_2^-$) and potassium iodide (KI), and FIG. 19 is a graph showing the analytical curve of nitric acid ions ($NO_3^-$) and titanium trichloride ($TiCl_3$). As is seen from these graphs, in case of FIG. 18, the analytical curve showed a desired linearity (viz., desired transform-responsibility) at the range from 7 ppb to 1.4 ppm, while, in case of FIG. 19, the analytical curve showed a desired linearity (viz., desired transform-responsibility) at the range from 7 ppb to 14 ppm.

The accuracy of the measurement was as follows. That is, when measurement was carried out five times repeatedly on nitrous acid ions of 0.28 ppm, the coefficient of variation was 1.4%, and when similar measurement was carried out on nitric acid ions of 0.14 ppm, the coefficient of variation was 1.2%.

In order to check the accuracy of the method of the above-mentioned fourth embodiment, a conventional calorimetric method and a conventional ion exchange chromatography method were also carried out together with the method of the fourth embodiment on four types of test water. The results are shown in TABLE-1 and TABLE-2.

TABLE 1

| Test water | $NO_2^-$ (ppb) | |
|---|---|---|
| | Present Invention | Colorimetic Method |
| Ujigawa | 64 | 66 |
| Katsuragawa | 37 | 39 |
| Kizugawa | 15 | 14 |
| Kamogawa | 32 | 34 |

TABLE 2

| Test water | $NO_3^-$ (ppm) | |
|---|---|---|
| | Present Invention | Ion Exc. Chromato. |
| Ujigawa | 1.4 | 1.4 |
| Katsuragawa | 4.2 | 4.3 |
| Kizugawa | 2.2 | 2.0 |
| Kamogawa | 2.0 | 2.0 |

As is seen from these tables, the method of the invention and the conventional methods showed substantially the same results.

Figure 20:
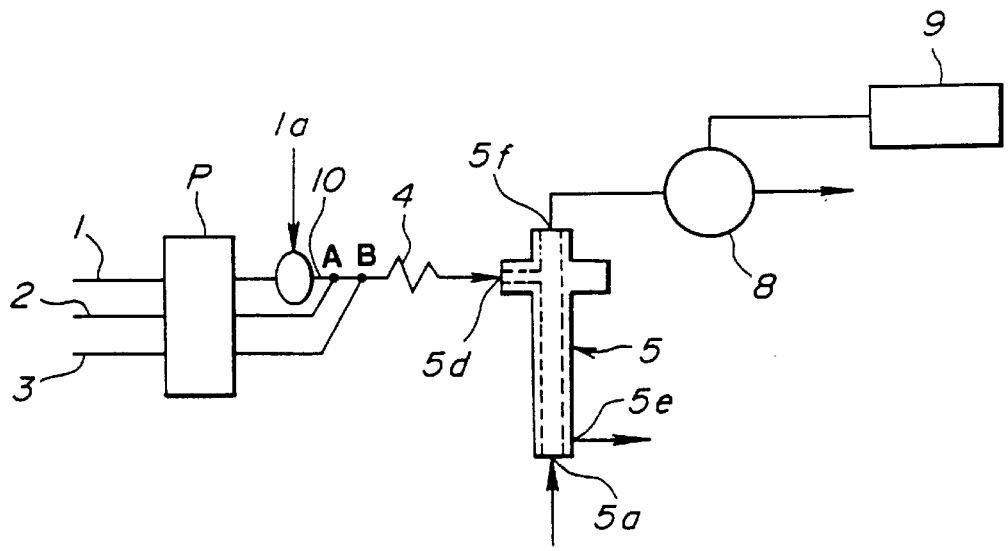
FIG. 20 is a first modification of the analyzing device of the fourth embodiment.

Referring to FIG. 20, there is shown a first modification of the analyzing device of the above-mentioned fourth embodiment.

In this modification, a countercurrent type "NO" gas separator 5 is employed in place of the membrane type separator 5. Similar to the membrane type separator 5, the countercurrent type "NO" gas separator 5 comprises a reacted solution inlet opening 5d, a clean air inlet opening 5a, a waste discharge opening 5e and a NO gas outlet opening 5f. In the separator 5, during the time when the reacted solution from the mixing coil 4 is flowing down along an outer surface of a tube, the clean air is led into the tube from the clean air inlet opening 5a. With this, NO gas is discharged from the reacted solution and led to the detector 8.

Figure 21:
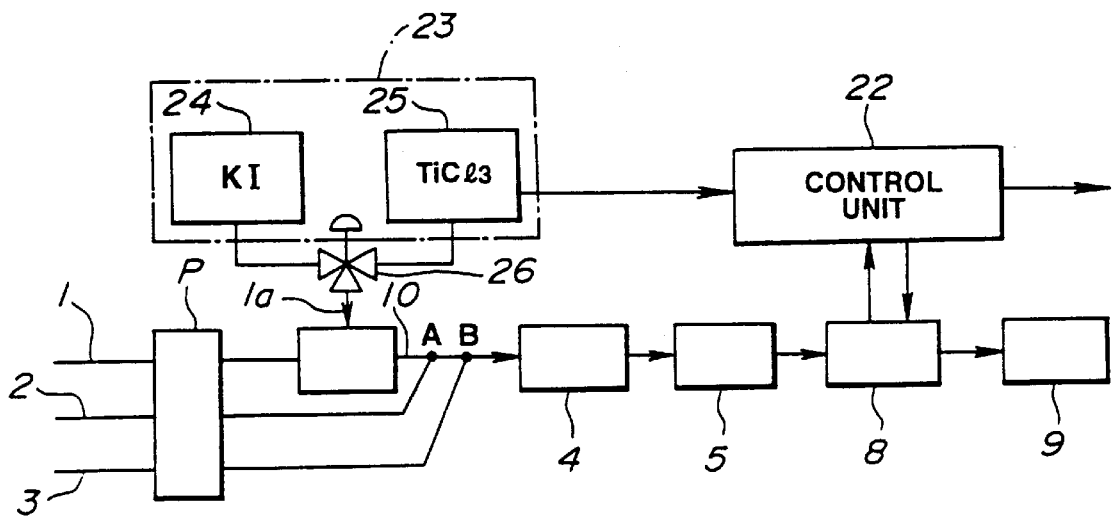
FIG. 21 is a second modification of the analyzing device of the fourth embodiment.

Referring to FIG. 21, there is a second modification of the analyzing device of the above-mentioned fourth embodiment.

In this modification, connected to the reagent inlet opening 1a of the pipe 10 is a reagent feeding mechanism 23. The mechanism 23 comprises a tank 24 for potassium iodide (KI) and a tank 25 for titanium trichloride ($TiCl_3$) which are connected to the reagent inlet opening 1a through a three-way electromagnetic valve 26. Designated by numeral 22 is a control unit.

In operation, by manipulating the valve 26, the potassium iodide (KI) and the titanium trichloride ($TiCl_3$) are selectively fed to the reagent inlet opening 1a. With this, based on the above-mentioned measuring process, the nitric acid ions ($NO_3^-$) and the nitrous acid ions ($NO_2^-$) can be continuously estimated.

What is claimed is:

1. A method for estimating selectively both nitric acid ions and nitrous acid ions in a sample solution, by using a common analyzing device, comprising the steps of:

(a) feeding both the sample solution and a reducing agent to an acidic solution which is flowing in a pipe;

(b) feeding clean air to the acidic solution which has the sample solution and the reducing agent contained therein;

(c) positively mixing the sample solution and the reducing agent under existence of the clean air in a mixing coil installed in said pipe thereby to produce a reacted solution;

(d) leading the reacted solution to a membrane type gas/liquid separator to separate a gaseous phase from the reacted solution, said separator being inclined by an angle "θ" with respect to a horizontal line and arranged to be rotatable about an axis of said separator; and (e) estimating the nitric acid ions and nitrous acid ions in the gaseous phase, the estimation being made by using chemiluminescence detection technique, wherein at the step (a), greater than 5% titanium trichloride solution is used as the reducing agent when the ions which are to be estimated are nitric acid ions, and wherein 0.1% to 20% potassium iodide solution is used as the reducing agent when the ions which are to be estimated are nitrous acid ions.

2. A method as claimed in claim 1, wherein said separator is of a countercurrent type.

3. A method as claimed in claim 1, wherein the concentration of said titanium trichloride solution is 20%.

4. A method as claimed in claim 1, wherein said acidic solution flowing in said pipe is a sulfuric acid solution.

5. A method as claimed in claim 1, wherein said acidic solution flowing in said pipe is 1N to 2N-sulfuric acid solution, the concentration of said titanium trichloride solution is 20%, and the concentration of said potassium iodide solution is 10%.

6. A method as claimed in claim 1, wherein at least one of the steps (a),(b),(c),(d) and (e) are automatically carried out.

* * * * *